(12) United States Patent
Häussermann et al.

(10) Patent No.: US 11,664,104 B2
(45) Date of Patent: May 30, 2023

(54) INHALER TRAINING SYSTEM AND METHOD

(71) Applicant: VisionHealth GmbH, Garching b. Munich (DE)

(72) Inventors: Sabine Häussermann, Neuried (DE); Alexandros Sivris, Munich (DE); Jonas Benedikt Natzer, Munich (DE)

(73) Assignee: VisionHealth GmbH, Garching bei Munich (DE)

( * ) Notice: Subject to any disclaimer, the term of this patent is extended or adjusted under 35 U.S.C. 154(b) by 254 days.

(21) Appl. No.: 16/955,802

(22) PCT Filed: Dec. 21, 2018

(86) PCT No.: PCT/EP2018/086541
§ 371 (c)(1),
(2) Date: Jun. 19, 2020

(87) PCT Pub. No.: WO2019/122315
PCT Pub. Date: Jun. 27, 2019

(65) Prior Publication Data
US 2021/0110905 A1  Apr. 15, 2021

(30) Foreign Application Priority Data
Dec. 21, 2017 (EP) ................................. 17209861

(51) Int. Cl.
*G16H 20/13* (2018.01)
*G06T 7/215* (2017.01)
(Continued)

(52) U.S. Cl.
CPC .......... *G16H 20/13* (2018.01); *G06F 18/214* (2023.01); *G06F 18/251* (2023.01); *G06N 3/08* (2013.01);
(Continued)

(58) Field of Classification Search
None
See application file for complete search history.

(56) References Cited

U.S. PATENT DOCUMENTS

2002/0140694 A1   10/2002   Sauer et al.
2005/0251030 A1   11/2005   Azar et al.
(Continued)

FOREIGN PATENT DOCUMENTS

CN   104834946 A   8/2015
JP   2016526193 A   9/2016

OTHER PUBLICATIONS

Written Opinion of International Application No. PCT/EP2018/086541, dated Jun. 3, 2019, 12 pages.

*Primary Examiner* — Vikkram Bali
(74) *Attorney, Agent, or Firm* — Pharma Patents International AG; Lily Ackerman

(57) ABSTRACT

The invention relates to a method and system for providing feedback to a patient using an inhaler of a specific type for inhaling a therapeutic aerosol according to instructions for use provided to the patient with the inhaler. The method comprises the steps of obtaining a sequence of digital audio signals and a sequence of digital video signals emitted from the patient while using the inhaler, recognising the type of the inhaler by processing the video signals, recognising whether the patient has deviated from the instructions by processing the audio and video signals, and recognising the type of the deviation; and presenting to the patient one or more feedback messages indicating whether a deviation was recognised, and if so, what type of deviation occurred, and optionally an inhalation manoeuvre without the deviation.

14 Claims, 2 Drawing Sheets

(51) Int. Cl.
*G06T 7/11* (2017.01)
*G06N 3/08* (2023.01)
*G06T 7/00* (2017.01)
*G06T 11/00* (2006.01)
*G06V 20/40* (2022.01)
*G06V 40/20* (2022.01)
*G06F 18/214* (2023.01)
*G06F 18/25* (2023.01)

(52) U.S. Cl.
CPC .............. *G06T 7/0012* (2013.01); *G06T 7/11* (2017.01); *G06T 7/215* (2017.01); *G06T 11/00* (2013.01); *G06V 20/40* (2022.01); *G06V 40/28* (2022.01); *G06T 2207/10016* (2013.01); *G06T 2207/30061* (2013.01)

(56) References Cited

U.S. PATENT DOCUMENTS

| | | |
|---|---|---|
| 2013/0063579 A1 | 3/2013 | Hanina et al. |
| 2014/0184772 A1* | 7/2014 | Hanina ............... G16H 30/40 348/77 |
| 2017/0160549 A1 | 6/2017 | Badiali et al. |
| 2017/0238842 A1 | 8/2017 | Jacquel et al. |
| 2017/0323062 A1 | 11/2017 | Djajadiningrat et al. |
| 2018/0092595 A1* | 4/2018 | Chen ................... A61M 15/00 |

* cited by examiner

INHALER TRAINING SYSTEM AND METHOD

CROSS REFERENCE TO RELATED APPLICATIONS

This application is a United States National Stage Application filed under 35 U.S.C. § 371 claiming priority to and the benefit of PCT Application No. PCT/EP2018/086541, filed on Dec. 21, 2018, which claims priority to and the benefit of European Application No. 17209861.8, filed on Dec. 21, 2017, all of which are incorporated herein by reference in their entireties.

BACKGROUND OF THE INVENTION

Respiratory patients receive most of their drug via inhalation devices. That way, the drug reaches the lungs directly, which is the target region to be treated. The known problem is that the market of inhalation devices is growing and therefore the variety. There are at least 4 different categories of devices which support inhalation of pharmaceuticals into the lung: dry powder inhalers, nebulizers, metered dose inhalers (MDI) and soft mist inhalers. They all meant to be used for the self-administration of the drugs for the patient at home.

When drugs are administered as tablets, only adherence is crucial for the success of the therapy. With inhaled drugs, not only the regular use of the drug, but the proper handling of the inhalation device and the inhalation manoeuvre are crucial. If the inhalation is not performed properly, the amount of administered drug to the lung is too low for the therapeutic success. The chronic disease, like Asthma or COPD, is more likely to be unstable, patients are prescribed higher doses unnecessarily or end up in hospital more frequently. Therefore, patients need guidance to the proper use of the inhalation system.

In MDIS for example, the release of the pharmaceuticals needs to be aligned with the start of inhalation or the inhalation with dry powder inhalers needs to be swift and forceful. Some of the devices have to be held upright or in another defined angle in order to release the full amount of drug.

The wrong use of inhaled therapy is common according to the literature, but can be avoided through proper and repeated education and training of the patient. Such training approaches comprise the provision of films and other illustrating manuals to the patient as well as additional assistive equipment and devices which measure the outcome during the use of an inhaler. The devices constitute specific constructions for example with sensors coupled to a patient and related computer processed feedback mechanism.

For example, in US 2015/0339953 A1 a self-learning system is provided giving guidance to inhaler systems using a portable computer device and a camera device. The system comprises guidance of multiple stages of real-time learning, for example simultaneous viewing of the instructional video and the patient's real-time video.

In US 2013/0063579 A1, a training method is described which can train a patient to use a predetermined inhalation system. The system is specifically adapted per patient and inhaler. A universally applicable system would be more efficient.

Existing methods for inhalation training either lack personal interaction with the patient or come together with the requirement of additional equipment and are therefore, not portable. Therefore, there is a need for personalised and convenient training methods for patients using inhalation devices.

SUMMARY OF THE INVENTION

In a first aspect, the invention relates to a computer-implemented method for providing feedback to a patient using an inhaler of a specific type for inhaling a therapeutic aerosol according to instructions for use provided to the patient for, or along with, the inhaler. The method comprises the steps of (a) obtaining a sequence of digital audio signals and a sequence of digital video signals emitted from the patient while using the inhaler; (b) recognising the type of the inhaler by processing the video signals; (c) recognising whether the patient has deviated from the instructions by processing the audio and video signals; (d) if a deviation was recognised in step (c), recognising the type of the deviation; and (e) presenting to the patient one or more feedback messages indicating (i) whether a deviation was recognised; (ii) if a deviation was recognised, the type of deviation; and optionally (iii) an inhalation manoeuvre without the deviation.

In a further aspect, the invention provides a data processing system which comprises a processor adapted to carry out the method as described herein.

In yet a further aspect, the invention provides a computer programme comprising instructions which, when the programme is executed by a computer, cause the computer to carry out the steps of the method described herein.

According to a yet a further aspect, the invention provides a computer-readable storage medium comprising instructions which, when executed by a computer, cause the computer to carry out the steps of the method of the invention.

DETAILED DESCRIPTION OF THE INVENTION

Figure 1:
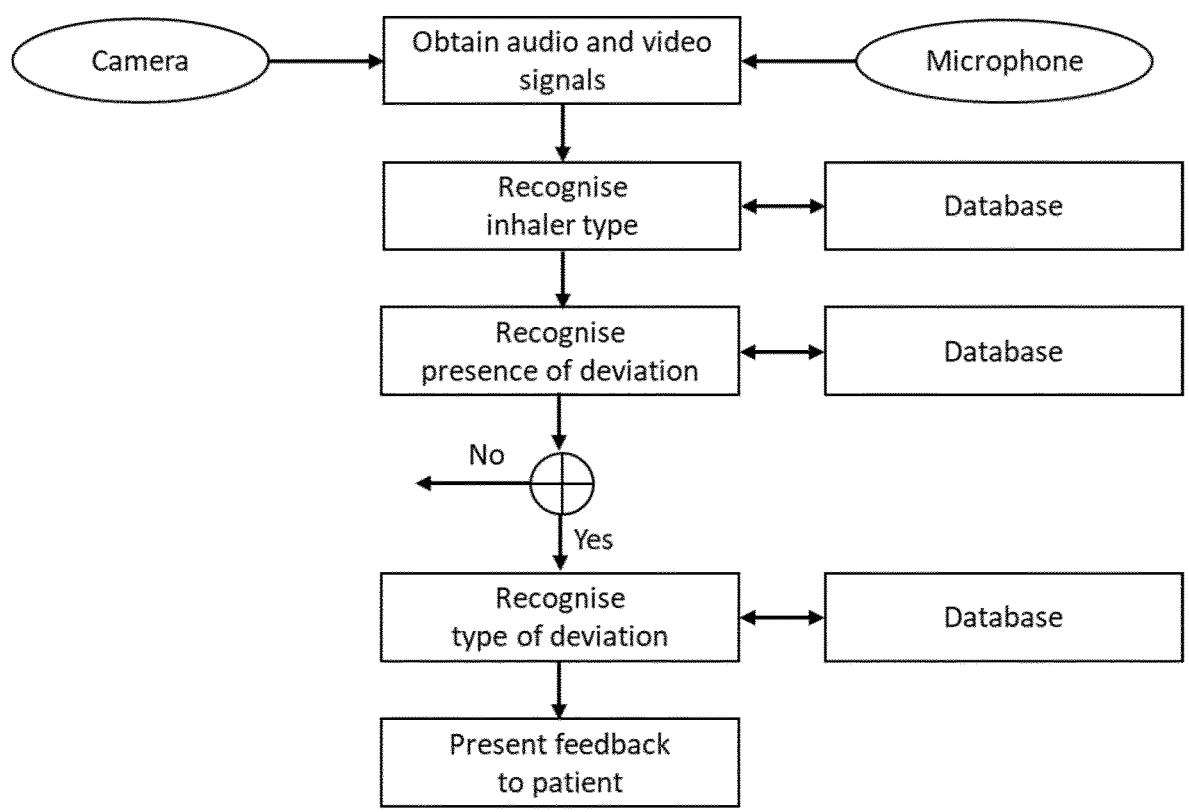
FIG. 1 represents a diagram illustrating the steps of the method of the invention according to a first embodiment.
Figure 2:
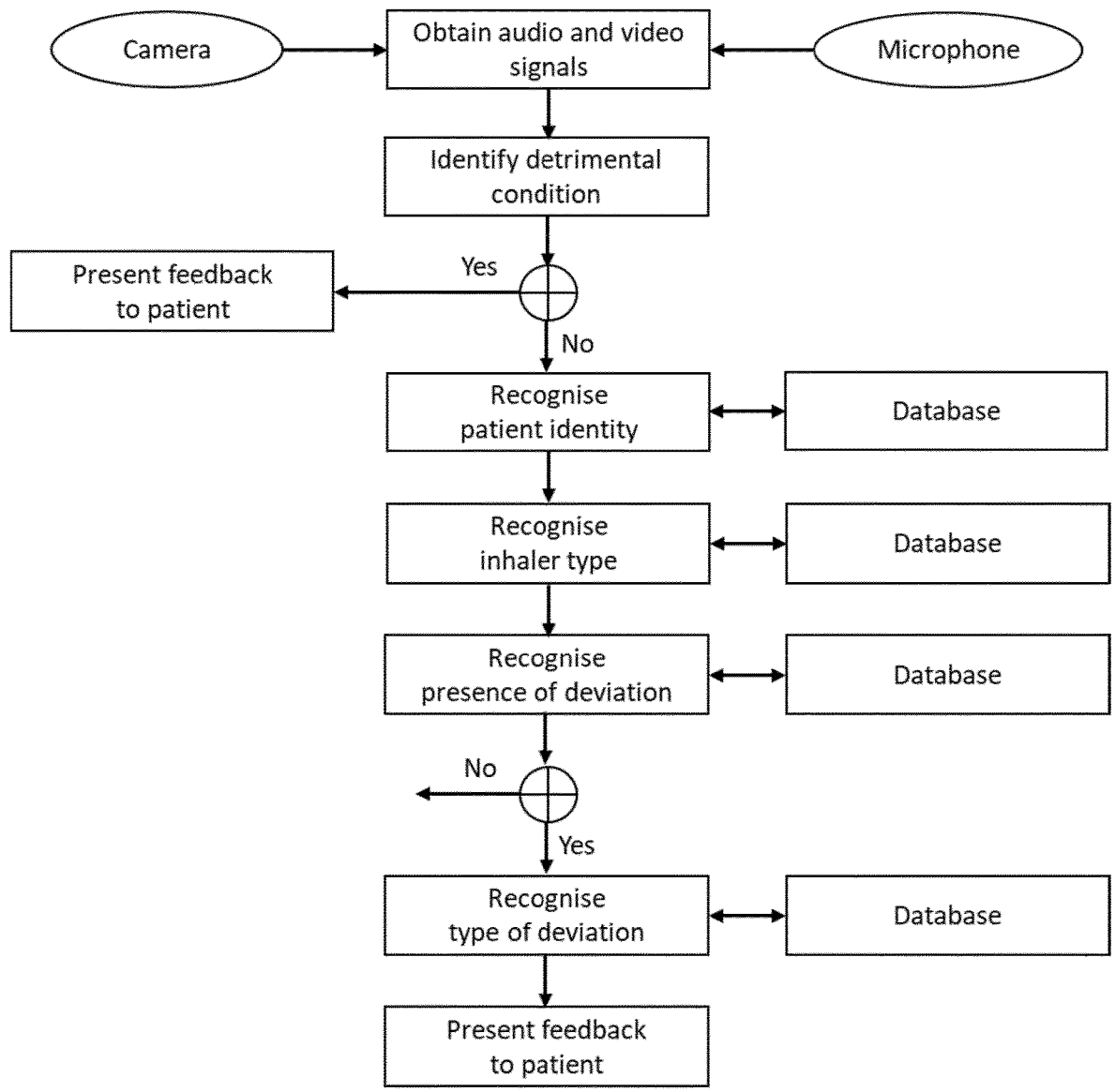
FIG. 2 represents a diagram illustrating the steps of the method of the invention according to a further optional embodiment.

In a first aspect, the invention provides a computer-implemented method for providing feedback to a patient using an inhaler of a specific type for inhaling a therapeutic aerosol according to instructions for use provided to the patient along with the inhaler as defined in claim 1.

In one embodiment, the method comprises the steps of:
(a) obtaining a sequence of digital audio signals and a sequence of digital video signals emitted from the patient while using the inhaler;
(b) recognising the type of the inhaler by processing the video signals;
(c) recognising whether the patient has deviated from the instructions by processing the audio and video signals;
(d) if a deviation was recognised in step (c), recognising the type of the deviation; and
(e) presenting to the patient one or more feedback messages indicating
(i) whether a deviation was recognised;
(ii) if a deviation was recognised, the type of deviation; and optionally (iii) an inhalation manoeuvre without the deviation; wherein preferably steps b) and c) are performed by analysing the video and audio signals using an artificial neural network trained to identify an inhaler type and to identify deviations, or by a method to detect a regular motion; wherein steps (a) to (e) are performed by a portable feedback device for handheld use comprising a data processing system;
a data memory;
a camera;
a microphone;
a display; and
a speaker.

Preferably, steps b) and c) comprise performing an analysis of the video and audio signals using an artificial neural network trained to identify an inhaler type and to identify deviations, and step c) also comprises the use of a method to detect a regular motion.

As used herein, an inhaler is an inhalation device capable of emitting a therapeutic aerosol such as to enable a user or patient to inhale the aerosol. An aerosol is a dispersion of a solid, semisolid or liquid phase in a continuous gaseous phase, thus including e.g. powder aerosols—pharmaceutically known as powders for inhalation—and nebulised aerosols. Inhalation devices for delivering powder aerosols are commonly described as powder inhalers. Aerosolised liquids are administered by means of various inhalation devices including nebulisers, pressurised metered-dose inhalers, and soft mist inhalers. In one embodiment, the method of the invention provides feedback to a patient using a powder inhaler, a nebuliser, a metered-dose inhaler or a soft mist inhaler.

A major advantage of the method according to the invention is the possibility to perform the method on a handheld device. A suitable handheld device may be a smartphone. The method in general can be performed on any processor, even on a relatively slow processor such as smartphones or a raspberry pie. The present method can be performed in real time and does not require access to a server with much computational power, i.e. the method can be performed offline.

The inhaler type refers to the specific inhaler model or model family. In this context, a model family means those variants of a model which are used by a patient in essentially the same manner, in particular with respect to the breathing manoeuvre. For illustration, an example of a specific type of nebuliser is the PARI eFlow rapid nebuliser system, which is an electronic nebuliser incorporating a vibrating mesh technology; an example of a specific type of powder inhaler is the ADVAIR DISKUS® sold by GSK; an example of a specific type of soft mist inhaler is the SPIRIVA® RESPIMAT® sold by Boehringer Ingelheim; and an example of a specific type of metered-dose inhaler is VENTOLIN® HFA sold by GSK.

Each inhaler is provided to a patient together with instructions for use, which are typically printed on a patient leaflet, but which may also be provided to the patient through the internet or by oral and/or visual information received from a health care provider such as a physician, pharmacist or nurse.

The patient using the inhaler is a human subject who is in need of, or would benefit from, the therapeutic aerosol administered through the inhaler. The use may be for any medical purpose, including the prevention or treatment of any disease, condition or symptom for which the aerosol is potentially beneficial.

An advantage of the method of the invention is that the method identifies the inhaler type. Methods of the prior art, e.g as described in US 2013/0063579 A1 may be suitable to train a patient but require to be adapted to a specific inhaler beforehand.

The inhaler may be identified using a pre-trained artificial neural network. As such, the method may be performed on a handheld device with limited computing power, e.g. a smartphone.

The method of the invention is computer-implemented. Any suitable computer or other device comprising a data processing system, a data memory, means for obtaining audio and video signals and means for presenting audio and video feedback messages may be used for the purpose of carrying out the method, e.g. by installing software that, when executed by the data processing system of the device, causes the device to perform the method steps as described herein. In one of the preferred embodiments, the device is a portable feedback device. An example of a suitable device is portable and may be configured by means of a computer programme to carry out the steps of the invention is a smartphone.

The method comprises a step of obtaining a sequence of digital audio signals and a sequence of digital video signals emitted from the patient while using the inhaler. The audio signals may be obtained from a microphone, and the video signals may be obtained from a camera; the microphone and the camera may be incorporated within the portable feedback device. The relevant signals are emitted from the patient while using the inhaler, which includes the signals emitted from the inhaler itself during the use by the patient.

In one embodiment, the sequence of audio signals covers, or is collected over, the time during which the patient performs one breathing manoeuvre using the inhaler. In another embodiment, audio signals from two or more consecutive breathing manoeuvres are obtained or collected. As used herein, a breathing manoeuvre includes an inspiratory phase in which the patient breathes in, or inhales, aerosol emitted from the inhaler, and an expiratory phase in which the patient breathes out, or exhales. In some cases, the breathing manoeuvre further includes a phase during which the patient holds the breath, and neither inhales or exhales.

Similarly, the video signals may cover, or be collected over, the time during which the patient performs one breathing manoeuvre using the inhaler, and optionally the time during which the patient performs two or more consecutive breathing manoeuvres. In one of the preferred embodiments, the video signals include signals from the patient's face as well as the inhaler.

In one embodiment, the sequences of the audio signals and of the video signals are obtained simultaneously.

The method further comprises a step of recognising the type of the inhaler, which is performed by processing the video signals in the previous step. This step may be performed by using a frame from the video signal, which is suspected to capture an inhaler A, as an input to a pretrained neural network-based classifier. The classifier outputs x different values, where each value corresponds to the likelihood of detecting inhaler $A_i$, and i is a number from one to x corresponding to the inhaler type.

The method further comprises a step of recognising whether the patient has deviated from the instructions, which is carried out by processing the audio and video signals which were obtained in a previous step. In this context, a deviation relates to the way the patient uses, or has used, the inhaler for inhaling the therapeutic aerosol, and while the audio and video signals were obtained or collected.

This step may be carried out after the step of recognising the type of the inhaler. In part, it may also be carried out simultaneously with recognising the inhaler type.

A deviation from the instructions may relate, for example, to the posture of the patient, the position or orientation of the inhaler, or the breathing manoeuvre of the patient. With respect to the breathing manoeuvre, a deviation from the instructions may, for example, be represented by too fast or too slow inhalation, a too short or too long inspiration phase, the presence or absence of a phase of holding the breath, an incorrect timing of actuation of the inhaler, incorrect expiration (e.g. through the mouthpiece of the inhaler if the instructions provide otherwise, or vice versa) and the like.

A further deviation may be a wrong preparation of the inhaler. Some inhalers, in particular suspension aerosols in the form of metered-dose inhalers require shaking in order to provide an optimized suspension to be inhaled. For other inhalers or combinations of inhalers and drug products, a slow stirring of the (optionally reconstituted) active composition may be required.

The step of recognising whether the patient has deviated from the instructions may be carried out by processing the audio and video signals emitted from the patient such as to calculate the likelihood of whether (or not) the breathing manoeuvre performed by the patient conforms with a properly performed breathing manoeuvre according to the instructions applicable to the respective inhaler.

The inventors were able to develop a new method to identify if the inhaler was correctly prepared. Prior art methods are based on optical flow analysis, which requires substantial computational power and cannot be performed on a smartphone or low power processor in real time. The inventors developed a new method, which allows the identification of regular movement, i.e. shaking or stirring in real time on processors with limited power, e.g. smartphone processors.

The method is in general based on movement recognition. Any method suitable for the selected device may be utilized. In particular, the method is a method for detecting regular movement as defined below.

If a deviation has been recognised, the method further comprises a step of recognising the type of the deviation that occurred. Also this step involves the processing of the audio and video signals which were obtained in a previous step.

In a further step, one or more feedback messages are presented to the patient, indicating whether a deviation was recognised, and if so, the type of deviation which occurred. Optionally, the feedback includes information on an inhalation manoeuvre without the respective deviation and how it should be performed by the patient.

According to the invention, a feedback message may be presented to the patient in an audio and/or video format, e.g. through a speaker and/or display which may be part of a portable feedback device, such as the speaker and display of a smartphone that is configured to carry out the method of the invention. In one embodiment, the feedback message, or at least one of several feedback messages, is presented to the patient in an audio-visual format. Other formats may also be used in addition to audio and/or video formats, such as haptic feedback. In one embodiment said feedback message is presented using augmented reality.

For example, a feedback message in an audio format with an indication that a deviation has occurred may be presented as a specific sound having a "negative" connotation, such as an alarm sound; or it may be presented as a spoken word message. In a visual format, the feedback may include displaying a symbol, colour, or text message indicating the presence of a deviation. Optionally, a video clip may be displayed to convey this information.

Similarly, the indication of the type of the deviation may be presented as a feedback message in an audio format, a visual format, or a combined audio-visual format. In one of the preferred embodiments, and due to the higher complexity of this indication, the format of this feedback is audio-visual.

The optional feedback indicating the correct use of the inhaler and in particular the correct breathing manoeuvre according to the respective instructions may also be presented in any of the formats mentioned above. In a preferred embodiment, the format is audio-visual. In a particular preferred embodiment, the format is audio-visual using augmented reality.

As mentioned, steps (a) to (e) of the method may be performed by a portable feedback device for handheld use. Such device comprises at least a data processing system, a data memory, a camera, a microphone, a display and a speaker. In the context of the invention, "portable" in combination with "for handheld use" means that the feedback device can be held in the hand of the patient while the method is being performed. The device may be custom-made or generic, such as a smartphone. In order for it to be a feedback device according to the invention, it must be adapted to perform the method steps, which adaptation is achieved by a computer programme which is executed on the device, i.e. by the data processing system of the device, so that, when the programme is executed, the method steps (a) to (e) are carried out.

The computer programme may be stored in the data memory of the portable feedback device. The sequence of digital audio signals emitted from the patient may be obtained in step (a) by means of the microphone, and the digital video signals by means of the camera of the device. The one or more feedback messages presented to the patient according to step (e) may be displayed on the display of the device, sounded through the speaker, or by using a combination of these output means.

The recognition of the inhaler type according to step (b) is based on the processing of the video signals, which may be performed by the data processing system of the device. The predefined inhaler shape parameters $A_1$ to $A_x$ may be stored in a database in the data memory of the feedback device. Alternatively, parameters $A_1$ to $A_x$ may be stored in a database which is stored in a remote memory or data storage device (e.g. cloud based), which is accessible by the data processing system preferably by wireless communication. Accordingly, it is preferred that the feedback device comprises a means for wireless communication with such external data memory or data storage device, optionally via the internet.

Similarly, the recognition of the presence and type of a deviation from the instructions by the patient in using the inhaler according to steps (c) and (d) may be carried out by the data processing system of the device, on which the computer programme is executed. Again, the pre-existing data based on which the data processing system recognises the deviation in the patient's breathing manoeuvre may be stored in the data memory of the feedback device, or may be obtained from an external data memory or data storage device which is preferably accessed by the feedback device by means of wireless communication.

As described above, one or more feedback messages are presented to the patient, indicating whether a deviation was recognised, and if so, the type of deviation which occurred. Optionally, the feedback includes information on an inhalation manoeuvre without the respective deviation and how it should be performed by the patient. The feedback message may be presented to the patient in an audio and/or video format, e.g. through a speaker and/or display which may be part of a portable feedback device, such as the speaker and display of a smartphone that is configured to carry out the method of the invention.

In one embodiment, said feedback messages are presented using augmented reality.

Optionally, the method comprises a further step of recognising the identity of the patient on the basis of video signals. This step may also be performed by the data processing system of the portable feedback device which is configured such as to obtain video signals from the camera, to process these signals and to compare them with stored data corresponding to specific faces. Again, the database in which such data are stored may be located in the data memory of the portable feedback device, or it may be located on an external data memory or data storage device which is preferably accessed by the feedback device by means of wireless communication.

The timing of this step is somewhat flexible. Its performance requires the availability of the sequence of digital video signals emitted from the patient, but not necessarily while using the inhaler. Thus, the recognition of the identity of the patient could even be carried out before step (a) or after step (e). Optionally, however, the identity of the patient is recognised by processing the sequence of digital video signals emitted from the patient while using the inhaler, as provided according to step (a), and the recognition itself may be performed at least partially in parallel to step (a), or simultaneously with steps (b), (c), and/or (d).

If the identity of the patient is recognised, the method may comprise a further optional step of presenting a feedback message to the patient indicating the fact that the patient has been recognised or identified, or indicating the identity of the patient that has been recognised. Like the other feedback messages, such message regarding the identity of the patient may be presented in an audio and/or video format, e.g. through a speaker and/or display which may be part of a portable feedback device, such as the speaker and display of a smartphone that is configured to carry out the method of the invention. For example, the name of the patient may be displayed in writing, or a vocal message indicating the name may be sounded via the speaker, or an image of the face of the patient may be displayed, or any combinations thereof.

In one embodiment, the feedback message indicating the fact that the patient has been recognised or identified, or indicating the identity of the patient that has been recognised, is presented before the presentation of the one or more feedback messages indicating whether a deviation was recognised and the type of deviation, if any. In another embodiment, the feedback message regarding the patient identity is presented at least partially in parallel (or simultaneously) with one or more other feedback messages of step (e).

Furthermore, the method may optionally comprise a step of identifying whether a detrimental condition capable of adversely affecting the quality of the audio signals or of the video signals is present, and optionally, identifying the nature and magnitude of such detrimental condition. As used herein, a detrimental condition should be interpreted broadly such as to include environmental conditions as well as the handling of the portable feedback device by the patient, or combinations of both.

In one embodiment, the detrimental condition is an environmental condition. For example, such environmental condition may relate to a particularly low or high luminous intensity prevailing when the patient is about to use the inhaler. A detrimental environmental condition co-affected by the patient (e.g. by the way in which the patient holds the inhaler and/or the portable feedback device) is the luminance contrast in the video signals emitted from the patient. If this is very high, the performance of steps (b), (c) and/or (d) as well as the optional step of recognising the identity of the patient based on the video signals may be difficult or—in extreme cases—impossible.

Another example of a detrimental environmental condition is the presence of acoustic noise, i.e. unwanted sound that is not related to the use of the inhaler by the patient. For example, the average acoustic background noise should preferably be lower than about 50 dB, and more preferably lower than about 40 dB, or lower than about 35 dB. In one of the particularly preferred embodiments, the threshold value is about 30 dB, above which the presence of a detrimental environmental condition is recognised.

An example of a detrimental condition caused by the patient is the shaking of the portable feedback device. A shaking frequency of about 1 Hz or more, or of about 2 Hz or more, or in particular a shaking frequency of about 3 Hz or more, may make it difficult to obtain a sufficiently high quality of video signals allowing the performance of steps (b) to (d), or the recognition of the identity of the patient. Each of these shaking frequencies may serve as a threshold value above which the presence of a detrimental condition is recognised.

If a detrimental condition capable of adversely affecting the quality of the audio signals or of the video signals is identified, the method preferably comprises a further step of presenting to the patient a feedback message indicating the presence and optionally the nature of the detrimental condition. With respect to the options and preferences relating to the feedback message, its formats, and the means by which it is presented, reference is made to the above parts of the description which describe the presentation of other feedback messages, which should be applied in analogy. For example, a feedback message such as "too dark", "too much noise", or "please avoid shaking" may be displayed on the display or sounded via the speaker of the portable feedback device.

The method of the invention may further comprise a step of instructing the patient to inhale the therapeutic aerosol using the inhaler according to the instructions for use while the feedback device is operating and is held such that the camera and the microphone are directed towards the patient's face. This step may be performed prior to step (a), and the respective instructions may be presented to the patient in various optional forms. For example, the instructions may be printed in a leaflet or manual distributed along with the portable feedback device if the device is a custom-made device, or along with the computer programme, if the device is generic (such as a smartphone) and configured to perform the method of the invention by means of such software. Alternatively, or in addition, the instructions may be displayed on the display or sounded through the speaker of the portable feedback device in the same manner as one of the feedback messages as described above.

In a further aspect of the invention, a data processing system is provided which comprises a processor adapted to carry out the method as described herein. As mentioned, the data processing system may be of a generic nature, such as the data processing system of a smartphone, which is adapted or configured to carry out the method steps by means of a computer programme which is loaded and executed on the data processing system. However, regardless of whether the device within which the data processing system is incorporated is generic or custom-made, it is preferred that the device is portable and suitable for handheld use, and further comprises a data memory, a camera, a microphone, a display, and a speaker.

In yet a further aspect, the invention provides a computer programme comprising instructions which, when the programme is executed by a computer, cause the computer to carry out the steps of the method described herein. Again, the computer preferably comprises the data processing system as defined above.

In yet a further aspect, the invention provides a computer-readable storage medium comprising instructions which, when executed by a computer, cause the computer to carry out the steps of the method of the invention. The computer-readable storage medium may be any type of data storage medium, i.e. an optical, magnetic, semiconductor-based or any other class of medium. It is preferably a non-volatile storage medium, such as a flash memory, a digital optical disc, a hard disc drive or a solid-state drive.

In a further aspect, the invention relates to a computer-implemented method to detect and/or analyse a regular motion comprising the steps of:
(a) obtaining a sequence of digital video signals emitted from said regular motion;
(b) in said video signals performing the following steps on a series of frames of said video signal:
 (i) selecting a portion of a frame through which said regular motion passes through;
 (ii) computing the mean brightness value within said portion of the frame;
 (iii) storing said mean brightness value of said portion of said frame in a buffer;
(c) repeating steps (i)-(iii) for a sequence of frames comprising a plurality of frames, wherein said portion of a frame is identical in each frame, creating a buffer of said mean brightness values;
(d) calculating the average of the mean brightness of all values determined and stored in said buffer of brightness values;
(e) subtracting said determined average of the mean brightness from each value in said buffer to generate a zero centered buffer;
(f) computing the zero crossing rate of said zero centered buffer.

The new method developed by the inventors is advantageous over the methods of prior art, as it allows a real time analysis even on slower, less powerful processors, e.g. smartphone processors or a raspberry pie.

Preferably said method steps (a) to (f) are performed by a computing system comprising at least
a data processing system;
a data memory.

In some embodiments said device additionally comprises a camera.

In some embodiments, the method steps (a) to (f) are performed by computing system comprising
a data processing system;
a data memory;
a camera;
a microphone;
a display; and
a speaker.

In a more preferred embodiment, said computing system is portable, more preferably portable and for handheld use. In some embodiments, In a particular embodiment said computing system is a smartphone.

Steps (i) to (iii) should be performed over a plurality of frames, covering at least 1 second of motion. Preferably, said steps are repeated for at least about 24 frames, or preferably for at least about 48 frames.

The method requires the selection of a portion of a frame. Said frame should cover part of the motion, i.e. the motion passes through the device, but is not completely performed inside said portion of the frame. Said portion of the frame should be the same for the analysis of the motion. Preferably, said portion of the frame is identical in each frame analyzed, preferably identical relative to the position of the regular movement. Preferably, the portion of the frame is corrected for camera movements, if the camera or video capture device is e.g. a handheld device.

In some embodiments said selection of a portion of a frame is adapted to adjust and correct for movement of the video capture device.

As already noted, the method is particularly suitable for computing systems with limited computational power, such as a smartphone. In order to improve the performance of the method, some further adjustment may be made to the method.

The method utilizes and stores the mean brightness values of said portion of a frame. Preferably, said brightness values are In some embodiments of the invention, the buffer to store the mean brightness values is a circular buffer.

The brightness values may be easier calculated if the video signal is converted into greyscale instead of full color. As such in some embodiments, the methods comprises in step (b) a further step prior to step (i):
(o) converting the color information of said frame to greyscale.

The method provides a zero-crossing rate, which is proportional to the strength or speed of the regular motion. As such, the speed or strength of the regular motion may be determined by comparison with a reference value.

Accordingly, in one embodiment, the invention relates to a method as defined above additionally comprising step (g):
(g) comparing the determined zero crossing rate with predetermined reference values to obtain an estimate on the speed or strength of said regular motion.

Further embodiments and optional feature will be apparent to a person skilled in the art.

The invention claimed is:
1. A computer-implemented method for providing feedback to a patient using an inhaler of a specific type for inhaling a therapeutic aerosol according to instructions for use provided to the patient for, or along with, the inhaler, the method comprising the steps of:
(a) obtaining a sequence of digital audio signals and a sequence of digital video signals emitted from the patient while using the inhaler;
(b) recognising the type of the inhaler by processing the video signals;
(c) recognising whether the patient has deviated from the instructions by processing the audio and video signals;
(d) if a deviation was recognised in step (c), recognising the type of the deviation; and
(e) presenting to the patient one or more feedback messages indicating
 (i) whether a deviation was recognised;
 (ii) if a deviation was recognised, the type of deviation; and optionally
 (iii) an inhalation manoeuvre without the deviation;
wherein steps b) and c) are performed by analysing the video and audio signals using an artificial neural network trained to identify an inhaler type and to identify deviations, or by a method to detect a regular motion;
wherein the deviation to be recognized in step (c) comprises a deviation from a regular movement using a method to detect a regular motion comprising the steps:
(I) perform the following steps on a series of frames of said video signals of the patient using the inhaler;
(i) optionally converting the color information of said frame to greyscale
(ii) selecting a portion of a frame through which said regular motion passes through;
(iii) computing the mean brightness value within said portion of the frame;
(iv) storing said mean brightness value of said portion of said frame in a buffer;
(II) repeating steps (i)-(iii) for a sequence of frames comprising a plurality of frames, wherein said portion of a frame is identical in each frame creating a buffer of brightness values;
(III) calculating the average of the mean brightness of all values determined and stored in said buffer of brightness values;
(IV) subtracting said determined average of the mean brightness from each value in said buffer to generate a zero centered buffer;
(V) computing the zero crossing rate of said zero centered buffer;
(VI) comparing the determined zero crossing rate with predetermined reference values to obtain an estimate on the speed or strength of said regular motion;
wherein said regular motion is shaking;
wherein steps (a) to (e) are performed by a portable feedback device for handheld use comprising
a data processing system;
a data memory;
a camera;
a microphone;
a display; and
a speaker.

2. The method of claim 1, wherein step c) is performed in real time on said portable feedback device and said feedback messages in step e) are presented immediately.

3. The method of claim 1, wherein in step e) said feedback messages are presented using augmented reality.

4. The method of claim 1, wherein the inhaler is a powder inhaler, a nebuliser, a metered-dose inhaler or a soft mist inhaler.

5. The method of claim 1, further comprising a step of recognising the identity of the patient on the basis of the video signals.

6. The method of claim 1, further comprising a step of identifying whether a detrimental condition capable of adversely affecting the quality of the audio signals or of the video signals is present, wherein the detrimental condition is optionally an environmental condition such as a luminous contrast or acoustic noise, or a patient activity such as shaking of the portable feedback device.

7. The method of claim 6, further comprising a step of presenting to the patient a feedback message indicating the presence and the nature of the detrimental condition.

8. The method of claim 1, further comprising a step of instructing the patient to inhale the therapeutic aerosol using the inhaler according to the instructions for use while the feedback device is operating and is held such that the camera and the microphone are directed towards the patient's face.

9. A data processing system comprising a processor adapted to carry out the method of claim 1.

10. A computer programme stored on a non-transitory computer-readable medium comprising instructions which, when the programme is executed by a computer, cause the computer to carry out the steps of the method of claim 1.

11. The computer programme stored on a non-transitory computer-readable medium of claim 10, wherein the computer comprises a data processing system comprising a processor adapted to carry out the steps of the method.

12. A non-transitory computer-readable storage medium comprising instructions which, when executed by a computer, cause the computer to carry out the steps of the method of claim 1.

13. The non-transitory computer-readable storage medium of claim 12, wherein the computer comprises a data processing system comprising a processor adapted to carry out the steps of the method.

14. A method of treatment of a disease, condition or symptom for which an aerosol is beneficial, to a patient using an inhaler of a specific type according to instructions for use provided to the patient for, or along with, the inhaler, the method comprising:
(a) obtaining a sequence of digital audio signals and a sequence of digital video signals emitted from the patient while using the inhaler to treat the disease, condition or symptom;
(b) recognising the type of the inhaler by processing the video signals;
(c) recognising whether the patient has deviated from the instructions by processing the audio and video signals;
(d) if a deviation was recognised in step (c), recognising the type of the deviation; and
(e) presenting to the patient one or more feedback messages indicating
(i) whether a deviation was recognised;
(ii) if a deviation was recognised, the type of deviation; and optionally
(iii) an inhalation manoeuvre without the deviation to treat the disease, condition or symptom;
wherein steps b) and c) are performed by analysing the video and audio signals using an artificial neural network trained to identify an inhaler type and to identify deviations, or by a method to detect a regular motion;
wherein the deviation to be recognized in step (c) comprises a deviation from a regular movement using a method to detect a regular motion comprising the steps:
(I) perform the following steps on a series of frames of said video signals of the patient using the inhaler;
(i) optionally converting the color information of said frame to greyscale
(ii) selecting a portion of a frame through which said regular motion passes through;
(iii) computing the mean brightness value within said portion of the frame;
(iv) storing said mean brightness value of said portion of said frame in a buffer;
(II) repeating steps (i)-(iii) fora sequence of frames comprising a plurality of frames, wherein said portion of a frame is identical in each frame creating a buffer of brightness values;
(II) calculating the average of the mean brightness of all values determined and stored in said buffer of brightness values;
(IV) subtracting said determined average of the mean brightness from each value in said buffer to generate a zero centered buffer;
(V) computing the zero crossing rate of said zero centered buffer;

(VI) comparing the determined zero crossing rate with predetermined reference values to obtain an estimate on the speed or strength of said regular motion;
wherein said regular motion is shaking;
wherein steps (a) to (e) are performed by a portable feedback device for handheld use comprising
a data processing system;
a data memory;
a camera;
a microphone;
a display; and
a speaker.

* * * * *